US009247945B2

(12) United States Patent  
Major et al.

(10) Patent No.: US 9,247,945 B2  
(45) Date of Patent: Feb. 2, 2016

(54) INSTRUMENT ASSEMBLY FOR IMPLANTING A STEM COMPONENT OF A KNEE PROSTHESIS AND ORTHOPAEDIC SURGICAL PROCEDURE FOR USING THE SAME

(71) Applicant: DEPUY (IRELAND), Cork (IE)

(72) Inventors: Lisa M. Major, Warsaw, IN (US); Rebecca L. Chaney, Warsaw, IN (US); Patrick J. Cannon, Warsaw, IN (US); Benjamin J. Sordelet, Fort Wayne, IN (US); Jonathan C. Lee, Warsaw, IN (US)

(73) Assignee: DEPUY (IRELAND) (IE)

( * ) Notice: Subject to any disclaimer, the term of this patent is extended or adjusted under 35 U.S.C. 154(b) by 193 days.

(21) Appl. No.: 13/793,072

(22) Filed: Mar. 11, 2013

(65) Prior Publication Data

US 2014/0257295 A1    Sep. 11, 2014

(51) Int. Cl.
| | |
|---|---|
| *A61B 17/16* | (2006.01) |
| *A61B 17/17* | (2006.01) |
| *A61B 19/00* | (2006.01) |
| *A61F 2/46* | (2006.01) |

(52) U.S. Cl.  
CPC .......... *A61B 17/1675* (2013.01); *A61B 17/164* (2013.01); *A61B 17/1764* (2013.01); *A61B 19/46* (2013.01); *A61B 2019/461* (2013.01); *A61B 2019/462* (2013.01); *A61F 2002/4658* (2013.01)

(58) Field of Classification Search  
CPC ...... A61B 17/16; A61B 17/17; A61B 17/164; A61B 17/1675  
USPC .............................. 606/79–85, 86 R, 88, 102  
See application file for complete search history.

(56) References Cited

U.S. PATENT DOCUMENTS

| | | | | |
|---|---|---|---|---|
| 5,429,504 | A * | 7/1995 | Peltier et al. .................. 433/165 |
| 6,258,095 | B1 * | 7/2001 | Lombardo et al. ............. 606/88 |
| 6,514,258 | B1 * | 2/2003 | Brown et al. .................. 606/80 |
| 6,517,581 | B2 * | 2/2003 | Blamey ...................... 623/22.12 |
| 8,246,621 | B2 * | 8/2012 | Poncet ............................ 606/79 |
| 8,449,546 | B2 * | 5/2013 | Ries ............................... 606/80 |
| 2006/0085005 | A1 * | 4/2006 | Kenealy et al. ................. 606/80 |
| 2010/0145345 | A1 * | 6/2010 | Ammann et al. ............... 606/88 |
| 2011/0166666 | A1 * | 7/2011 | Meulink et al. ............ 623/22.42 |
| 2013/0023881 | A1 * | 1/2013 | Cook et al. ..................... 606/80 |

FOREIGN PATENT DOCUMENTS

| | | |
|---|---|---|
| EP | 0947169 A2 | 10/1999 |
| EP | 1712194 A1 | 10/2006 |
| EP | 1714194 A1 | 10/2006 |
| WO | 2006039483 A2 | 4/2006 |
| WO | 2008036309 A2 | 3/2008 |

OTHER PUBLICATIONS

European Search Report for European Patent Application No. 14157141.4-1654, Jun. 16, 2014, 5 pages.

(Continued)

*Primary Examiner* — Christopher Beccia  
(74) *Attorney, Agent, or Firm* — Barnes & Thornburg, LLP (57) ABSTRACT

Surgical instruments for use in implanting a stem component into a knee of a patient include a canal reamer and an associated implant reference guide.

9 Claims, 8 Drawing Sheets

(56) References Cited

OTHER PUBLICATIONS

Zimmer NexGen LCCK, Surgical Technique for use with LCCK 4-in-1 Instrument, 2009, 52 pages.
DePuy Orthopaedics, Inc., Sigma Revision and M.B.T. Revision Tray, Surgical Technique, 2008, 82 pages.
Smith & Nephew, Legion, Revision Knee System, Surgical Technique, 2005, 40 pages.
Biomet, Vanguard SSK, Revision System, Surgical Technique, Feb. 2008, 64 pages.
GMK Revision, Surgical Technique, Ref. 99.27.12US rev. 1, 1999, 74 pages.
PFC Sigma RP-F, Specialist 2 Instruments, Surgical Technique, Performance in Flexion, 2007, 32 pages.
P.F.C. Sigma Rotating Platform Knee System with M.B.T Tray, Primary Procedure with a Curved or Posterior Stablised Implant, 2003, 43 pages.
LCS High Performance Instruments, Surgical Technique, 2008, 44 pages.
Sigma High Performance Instruments, Design Rationale, 2007, 12 pages.
Sigma High Performance Instruments, Classic Surgical Technique, 2010, 52 pages.
Attune Knee System Surgical Technique, 2013, 73 pages.

* cited by examiner

INSTRUMENT ASSEMBLY FOR IMPLANTING A STEM COMPONENT OF A KNEE PROSTHESIS AND ORTHOPAEDIC SURGICAL PROCEDURE FOR USING THE SAME

TECHNICAL FIELD

The present disclosure relates generally to instruments for implanting an orthopaedic prosthesis, and more particularly to instruments for implanting an orthopaedic knee prosthesis.

BACKGROUND

During the lifetime of a patient, it may be necessary to perform a joint replacement procedure on the patient as a result of, for example, disease or trauma. The joint replacement procedure may involve the use of a prosthesis which is implanted into one or more of the patient's bones. In the case of a knee replacement procedure, a tibial tray is implanted into the patient's tibia. A bearing is secured to the tibial tray. The condyle surfaces of a replacement femoral component bear against the tibial bearing.

Such a knee prosthesis may also include a number of elongated intramedullary stem components which are implanted in the patient's tibia and/or femur. To secure a stem component to the patient's tibia and/or femur, the intramedullary canal of the patient's tibia and/or femur is first surgically reamed such that the stem component may be subsequently implanted therein.

SUMMARY

According to one aspect, a surgical instrument for use during a surgical procedure to implant an orthopaedic knee prosthesis includes a surgical reamer having an elongated shank that includes a proximal end configured to fit into the chuck of a rotary power tool and a cutting head located at an opposite, distal end of the shank. The cutting head includes a cutting tip with a plurality of helical cutting flutes extending away from the cutting tip in a direction toward the proximal end of the elongated shank. The elongated shank of the surgical reamer also includes a plurality of depth marks formed in the helical cutting flutes of the cutting head, with each of the plurality of depth marks having an annular-shaped groove formed in the helical cutting flutes and is positioned at a location on the cutting head corresponding to a predetermined depth of operation of the surgical reamer.

In an embodiment, the plurality of depth marks includes a first depth mark, a second depth mark, and a third depth mark. The first depth mark has a different color than the second and third depth marks. The second depth mark is located between the first depth mark and the proximal end of the elongated shank, and the third depth mark is located between the first depth mark and the distal end of the elongated shank.

The plurality of depth marks further includes a fourth depth mark and a fifth depth mark, with the fourth depth mark being located between the second depth mark and the proximal end of the elongated shank, and the fifth depth mark being located between the third depth mark and the distal end of the elongated shank.

Each of the plurality of depth marks may have a different color than the other depth marks.

Each of the number of the plurality of depth marks may be filled with a colored epoxy ink.

In an embodiment, the annular-shaped groove formed in the helical cutting flutes of each of the plurality of depth marks extends around the entire circumference of the elongated shank.

According to another aspect, a surgical instrument assembly for use during a surgical procedure to implant an orthopaedic knee prosthesis includes a surgical reamer that includes an elongated shank having a proximal end configured to fit into the chuck of a rotary power tool and a cutting head located at an opposite, distal end of the shank. The cutting head includes a cutting tip with a plurality of helical cutting flutes extending away from the cutting tip in a direction toward the proximal end of the elongated shank. A plurality of depth marks are formed in the helical cutting flutes of the cutting head, with each of the plurality of depth marks being positioned at a location on the cutting head corresponding to a predetermined depth of operation of the surgical reamer. The surgical instrument assembly also includes an implant reference guide that includes an elongated guide body having a plurality of size marks located on the guide body. Each the plurality of size marks is positioned at a location on the guide body corresponding to a size and type of a surgical component of the orthopaedic knee prosthesis. A plurality of depth marks are formed in the guide body. The plurality of depth marks formed in the guide body of the implant reference guide correspond in quantity and spacing to the plurality of depth marks formed in the helical cutting flutes of the cutting head of the surgical reamer.

In an embodiment, the plurality of depth marks of the canal reamer includes a first depth mark, a second depth mark, and a third depth mark. The first depth mark has a different color than the second and third depth marks. The second depth mark is located between the first depth mark and the proximal end of the elongated shank, and the third depth mark is located between the first depth mark and the distal end of the elongated shank.

The plurality of depth marks of the implant reference guide includes a first depth mark, a second depth mark, and a third depth mark. The first depth mark of the implant reference guide has a different color than the second and third depth marks of the implant reference guide. The second depth mark of the implant reference guide is located between the first depth mark of the implant reference guide and a proximal end of the guide body, and the third depth mark of the implant reference guide is located between the first depth mark of the implant reference guide and an opposite, distal end of the guide body.

In an embodiment, the first depth mark of the surgical reamer is the same color as the first depth mark of the implant reference guide.

In an embodiment, each of the plurality of depth marks of the surgical reamer has a different color than the other depth marks of the surgical reamer, and each of the plurality of depth marks of the implant reference guide has a different color than the other depth marks of the implant reference guide.

In such an embodiment, each of the plurality of depth marks of the surgical reamer is the same color as one of the plurality of depth marks of the implant reference guide.

In an embodiment, each of the plurality of depth marks of the surgical reamer includes an annular-shaped groove formed in the helical cutting flutes of the surgical reamer.

In such an embodiment, the annular-shaped groove formed in the helical cutting flutes of each of the plurality of depth marks of the surgical reamer extends around the entire circumference of the elongated shank of the surgical reamer.

According to another aspect, a method of performing an orthopaedic surgical procedure to implant a prosthetic knee component into an end of a long bone of a knee of a patient includes determining a size of the prosthetic component to implant into the end of the long bone of the knee of the patient, and identifying a size mark corresponding to the determined size of the prosthetic component from a plurality of size marks located on an implant reference guide. The method also includes determining a depth mark, from a plurality of depth marks located on the implant reference guide, that is located closest to the size mark identified as corresponding to the determined size of the prosthetic component, and identifying a depth mark, from a plurality of depth marks located on a surgical reamer, that corresponds to the determined depth mark on the implant reference guide. The method also includes advancing the surgical reamer into the intramedullary canal of the long bone of the patient to a depth which corresponds to the identified depth mark on the surgical reamer.

In an embodiment, the method includes determining a size of a stem component to implant into a proximal end of a tibia of the patient, and advancing the surgical reamer into the intramedullary canal of the tibia of the patient to a depth which corresponds to the identified depth mark on the surgical reamer.

In another embodiment, the method includes determining a size of a stem component to implant into a distal end of a femur of the patient, and advancing the surgical reamer into the intramedullary canal of the femur of the patient to a depth which corresponds to the identified depth mark on the surgical reamer.

BRIEF DESCRIPTION OF THE DRAWINGS

The detailed description particularly refers to the following figures, in which.

DETAILED DESCRIPTION OF THE DRAWINGS

While the concepts of the present disclosure are susceptible to various modifications and alternative forms, specific exemplary embodiments thereof have been shown by way of example in the drawings and will herein be described in detail. It should be understood, however, that there is no intent to limit the concepts of the present disclosure to the particular forms disclosed, but on the contrary, the intention is to cover all modifications, equivalents, and alternatives falling within the spirit and scope of the invention.

Terms representing anatomical references, such as anterior, posterior, medial, lateral, superior, inferior, etcetera, may be used throughout this disclosure in reference to both the orthopaedic implants described herein and a patient's natural anatomy. Such terms have well-understood meanings in both the study of anatomy and the field of orthopaedics. Use of such anatomical reference terms in the specification and claims is intended to be consistent with their well-understood meanings unless noted otherwise.

Figure 1:
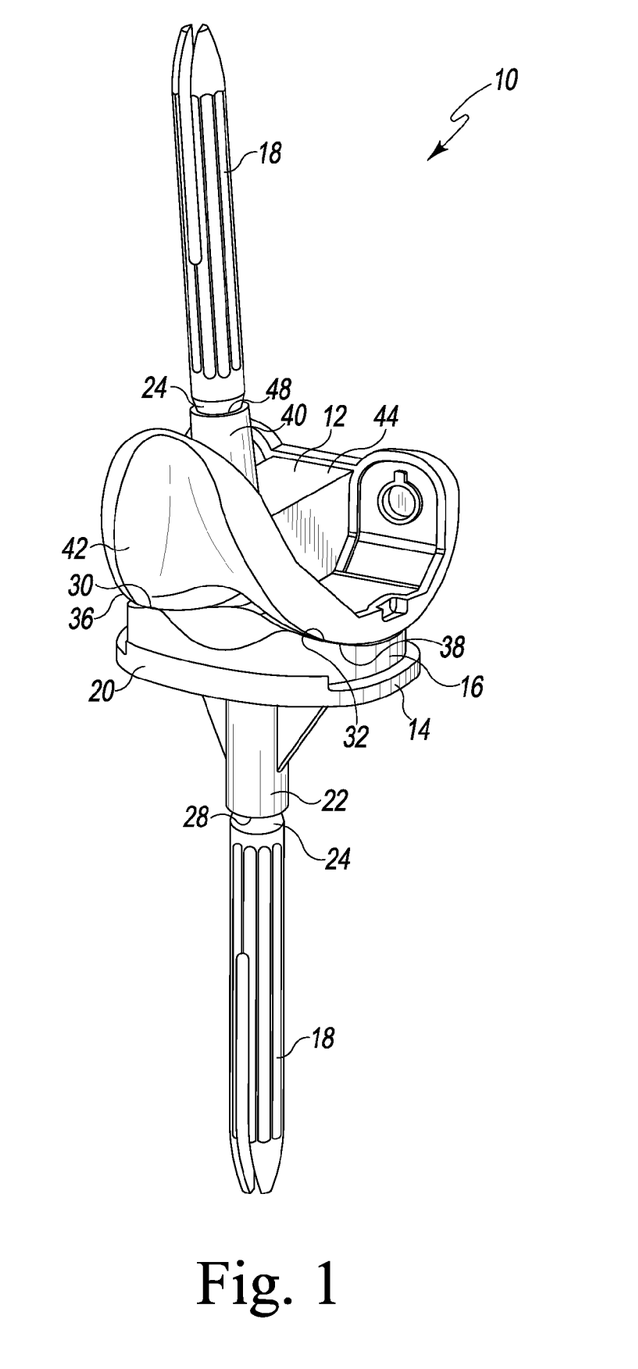
FIG. 1 is a perspective view of an orthopaedic knee prosthesis.

Referring now to FIG. 1, there is shown an implantable knee prosthesis 10 for use in the performance of an orthopaedic knee replacement procedure. The knee prosthesis 10 includes a femoral component 12, a tibial tray 14, a bearing 16, and a pair of stem components 18. One of the stem components 18 is secured to the tibial tray 14, with the other one being secured to the femoral component 12.

The tibial tray 14 is configured to be implanted into a surgically-prepared end of a patient's proximal tibia (not shown). The tibial tray 14 includes a platform 20 having an elongated stem post 22 extending inferiorly away from its inferior surface. The elongated tibial stem post 22 is configured to receive one of the stem components 18. Specifically, the tibial tray 14 has a tapered bore 28 formed therein into which a tapered post 24 of the stem component 18 may be advanced to taper lock the post 24 (and hence the stem component 18) and the tibial tray 14 to one another. In such a way, the stem component 18 may then be implanted into a surgically-reamed intramedullary canal of the patient's tibia.

The bearing 16 is securable to the tibial tray 14. In particular, the bearing 16 may be snap-fit to the tibial tray 14. In such a way, the bearing 16 is fixed relative to the tibial tray 14 (i.e., it is not rotatable or moveable in the anterior/posterior or medial/lateral directions). Although, in other embodiments, the tibial tray may be secured in a manner that allows it to rotate relative to the tibial tray 14.

The bearing 16 includes a lateral bearing surface 30 and a medial bearing surface 32. The bearing surfaces 30, 32 are configured to articulate with a lateral condyle surface 36 and a medial condyle surface 38, respectively, of the femoral component 12. Specifically, the femoral component 12 is configured to be implanted into a surgically-prepared distal end of the patient's femur (not shown), and is configured to emulate the configuration of the patient's natural femoral condyles. As such, the lateral condyle surface 36 and the medial condyle surface 38 are configured (e.g., curved) in a manner which mimics the condyles of the natural femur. The lateral condyle surface 36 and the medial condyle surface 38 are spaced apart from one another thereby defining an intercondylar notch therebetween.

Figure 2:
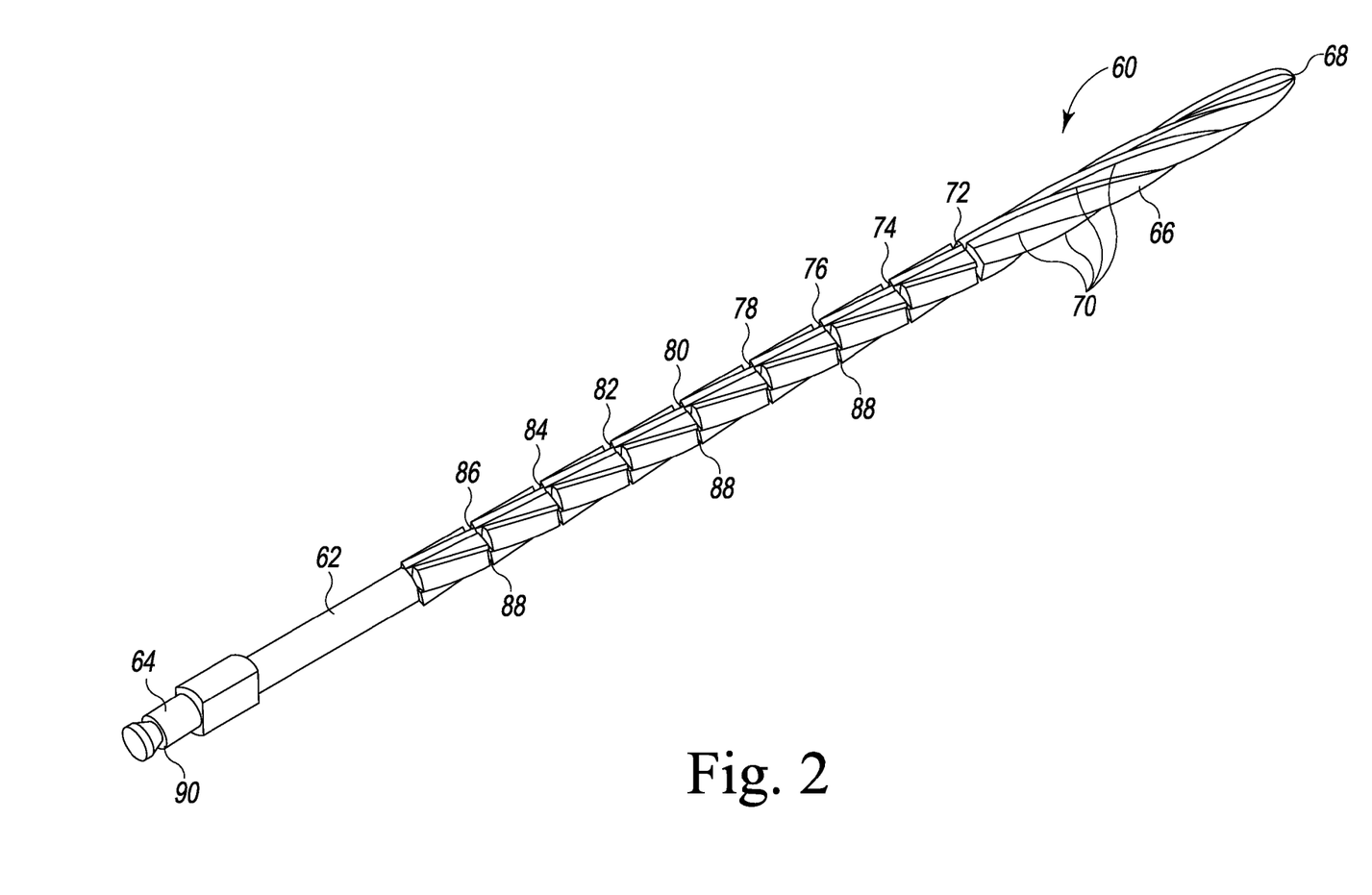
FIG. 2 is a perspective view of a canal reamer used in the surgical implantation of the orthopaedic knee prosthesis of FIG. 1.

The condyle surfaces 36, 38 are formed in a bearing surface 42 of the femoral component 12. The femoral component 12 also includes an elongated stem post 40, extending superiorly away from its opposite backside surface 44. The elongated femoral stem post 40 is configured to receive one of the stem components 18. Specifically, as can be seen in FIG. 1, the femoral component's stem post 40 has a tapered bore 48 formed therein into which a tapered post 24 of the stem component 18 may be advanced to taper lock the post 24 (and hence the stem component 18) and the femoral component 12 to one another (as shown in FIG. 2). In such a way, the stem component 18 may then be implanted into a surgically-reamed intramedullary canal of the patient's femur.

The components of the knee prosthesis 10 that engage the natural bone, such as the femoral component 12, the tibial tray 14, and the stem components 18 may be constructed with an implant-grade biocompatible metal, although other materials may also be used. Examples of such metals include cobalt, including cobalt alloys such as a cobalt chrome alloy, titanium, including titanium alloys such as a Ti6Al4V alloy, and stainless steel. Such a metallic components may also be coated with a surface treatment, such as hydroxyapatite, to enhance biocompatibility. Moreover, the surfaces of the metallic components that engage the natural bone may be textured to facilitate securing the components to the bone. Such surfaces may also be porous coated to promote bone ingrowth for permanent fixation.

The bearing 16 may be constructed with a material that allows for smooth articulation between the bearing 16 and the femoral component 12, such as a polymeric material. One such polymeric material is polyethylene such as ultrahigh molecular weight polyethylene (UHMWPE).

Referring now to FIGS. 2-11, there are shown a number of instruments used to implant the knee prosthesis 10 into the intramedullary canal of a long bone of the patient's knee (i.e., the patient's femur and/or tibia). In FIG. 2, there is shown a canal reamer 60 that may be used during the surgical preparation of the patient's femur and/or tibia. The canal reamer 60 is used to ream the portion of the patient's intramedullary canal into which the stem component 14 is implanted—i.e., either the intramedullary canal of the patient's femur or tibia. The canal reamer 60 includes an elongated shank 62 having a proximal end 64 that fits into the chuck of a rotary power tool. The canal reamer 60 also includes a cutting head 66 located at the opposite, distal end of the shank 62. The cutting head 66 of the canal reamer 60 includes a sharp cutting tip 68 with a plurality of helical cutting flutes 70 extending therefrom in the direction toward the proximal end 64 of the shank 62. When the canal reamer 60 is positioned in the intramedullary canal 22 of the patient's femur or tibia and rotated, the cutting head 66 reams or otherwise cuts the bone tissue of the femur thereby obtaining clear access to the canal. Such access to the intramedullary canal allows for implantation of the components of the knee prosthesis 10 such as the stem components 18.

Figure 3:
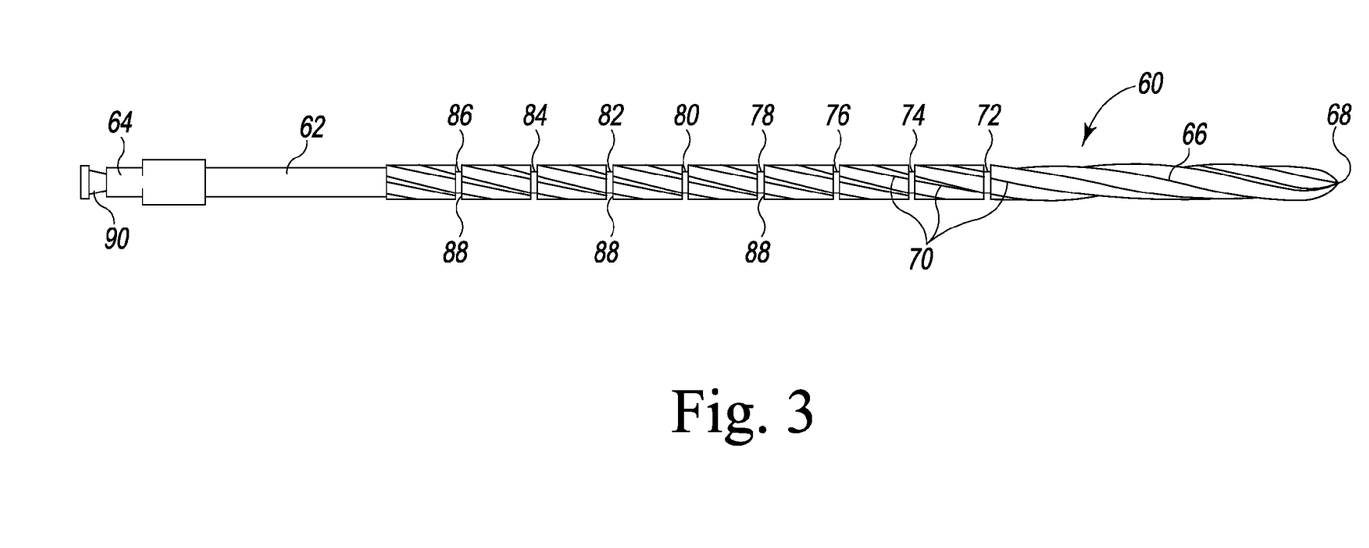
FIG. 3 is an elevation view of the canal reamer of FIG. 2.

The canal reamer 60 includes a number of depth marks 72, 74, 76, 78, 80, 82, 84, 86 formed in its cutting head 66. Each of the depth marks 72, 74, 76, 78, 80, 82, 84, 86 corresponds to a different depth to which the canal reamer 60 may be advanced to prepare the patient's intramedullary canal for one of a number of different stem components 18. As will be described below, an implant reference guide may be used to correlate a particular type and size of stem component 18 with one of the depth marks 72, 74, 76, 78, 80, 82, 84, 86.

The depth marks 72, 74, 76, 78, 80, 82, 84, 86 may be embodied as annular-shaped grooves 88 engraved or otherwise formed in the in the cutting head 66. As can be seen in FIG. 3, in the illustrative embodiment described herein, the grooves 88 extend around the entire circumference of the elongated shank 62. As such, each of the grooves 88 passes through the helically-shaped cutting flutes 70. As a result, the cutting flutes 70 form a cutting surface that is interrupted by the grooves 88 defining each of the depth marks 72, 74, 76, 78, 80, 82, 84, 86. Such deep grooves 88 allow the surgeon to quickly and easily identify the depth marks 72, 74, 76, 78, 80, 82, 84, 86 during use of the canal reamer 60. In particular, the depth of the grooves 88 allows the depth marks 72, 74, 76, 78, 80, 82, 84, 86 to be clearly visible when the canal reamer 60 is operated, even at relatively high speeds.

During a surgical procedure, the canal reamer 60 is advanced deeper into the intramedullary canal of the patient's femur or tibia until the desired depth mark 72, 74, 76, 78, 80, 82, 84, 86 aligns with a surgically-prepared outer surface of the patient's femur or tibia and clear access to the canal is achieved. In such a way, over reaming of the canal is avoided if the canal reamer 60 is not driven beyond the appropriate depth mark 72, 74, 76, 78, 80, 82, 84, 86.

In an illustrative embodiment, the depth mark 80 near the middle of the cutting head 66 may be colored (e.g., black) so as to distinguish it from the other depth marks 72, 74, 76, 78, 82, 84, 86. In such a way, the surgeon can use the center depth mark 80 as a quick reference guide for identifying the other depth marks 72, 74, 76, 78, 82, 84, 86. For example, the surgeon can quickly and easily identify the depth mark 74 as being "three depth marks below" the colored middle depth mark 80, or the depth mark 84 as being "two depth marks above" the colored middle depth mark 80.

Alternatively, each of the depth marks 72, 74, 76, 78, 80, 82, 84, 86 may be embodied in a different color than the other depth marks 72, 74, 76, 78, 80, 82, 84, 86. In other words, each of the depth marks 72, 74, 76, 78, 80, 82, 84, 86 may have a unique color.

In embodiments in which one or more of the depth marks 72, 74, 76, 78, 80, 82, 84, 86 are colored, the grooves 88 of the colored depth mark is filled with an epoxy ink of the desired color. Alternatively, a colored band may be installed in the grooves 88.

A male connector 90 is formed in the proximal end 64 of the shank 62 of the canal reamer 60. The connector 90 fits into the chuck of a rotary power tool to couple the canal reamer 60 to a rotary drive source.

To accommodate the various different configurations of the stem components 18, the canal reamer 60 may likewise be provided in a number of different configurations. In particular, the canal reamer 60 may be configured in various different diameters to produce a reamed bore of a size sufficient to receive the stem components 18 of various different diameters. In one illustrative embodiment, the canal reamer 60 may be provided in 1 mm diameter increments ranging from 8 mm to 24 mm (or the largest size of the stem component 18).

The canal reamer 60 may be constructed from a medical-grade metal such as stainless steel, cobalt chrome, or titanium, although other metals or alloys may be used. Moreover, in some embodiments, rigid polymers such as polyetheretherketone (PEEK) may also be used.

Referring now to FIGS. 4-11, there is shown a pair of implant reference guides that may be used by a surgeon to determine the proper depth to advance the canal reamer 60 for implantation of one of the stem components 18 into the intramedullary canal of the patient's tibia or femur. The implant reference guides may be constructed from rigid polymers such as polyetheretherketone (PEEK) or a medical-grade metal such as stainless steel, cobalt chrome, or titanium, although other metals or alloys may also be used.

Figure 4:
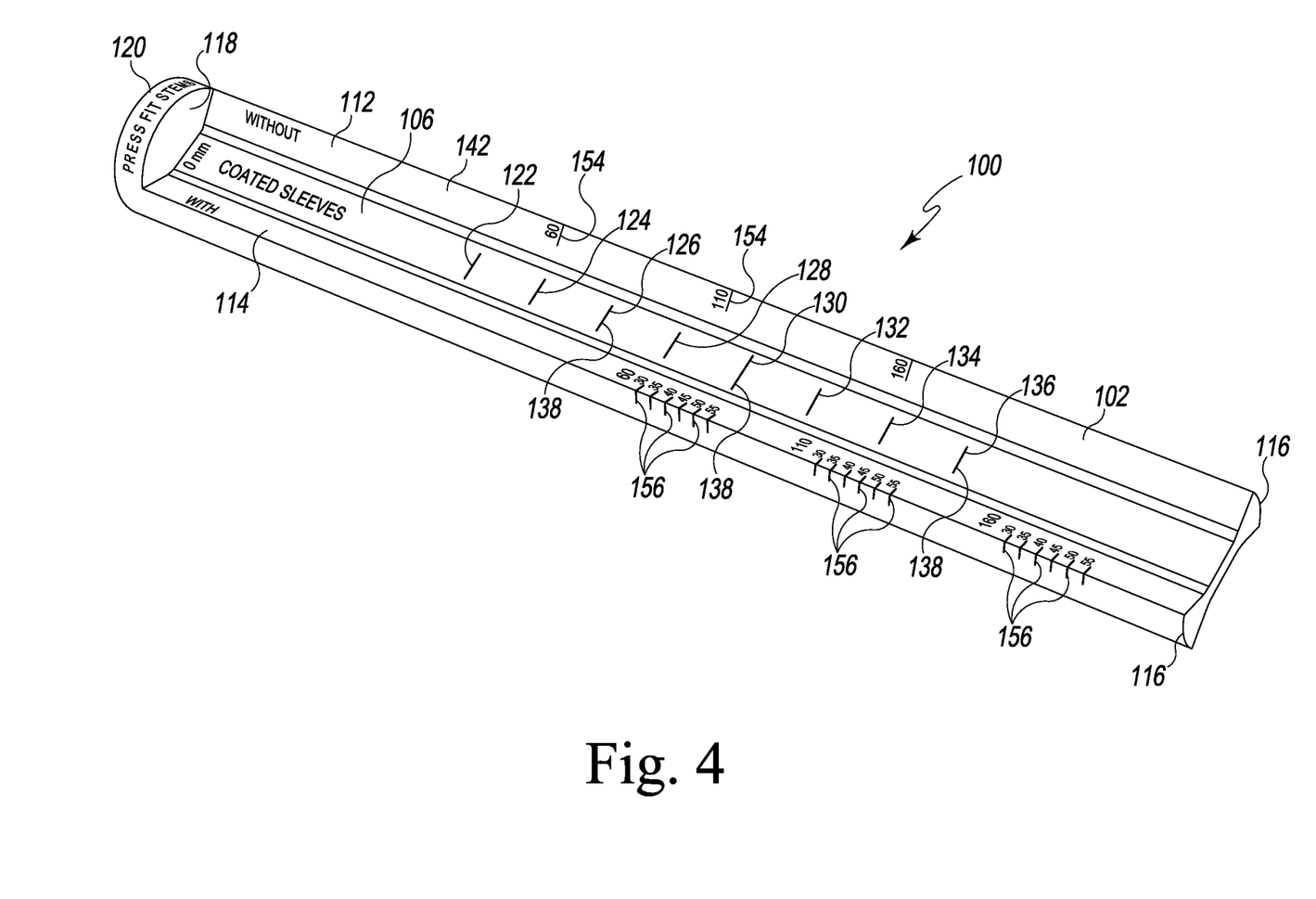
FIG. 4 is a perspective view of a femoral implant reference guide.
Figure 5:
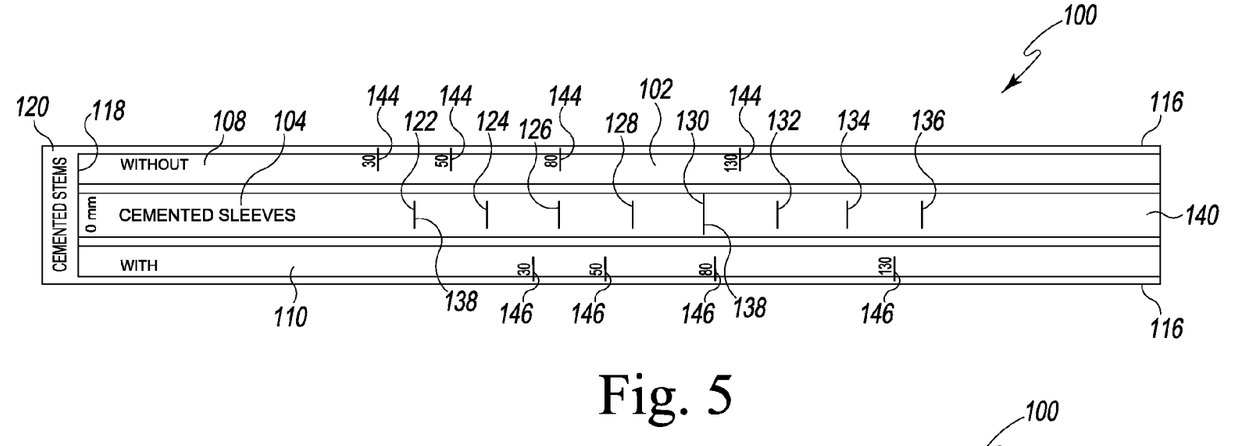
FIGS. 5 and 6 are side elevation views of the femoral implant reference guide of FIG. 4.
Figure 6:
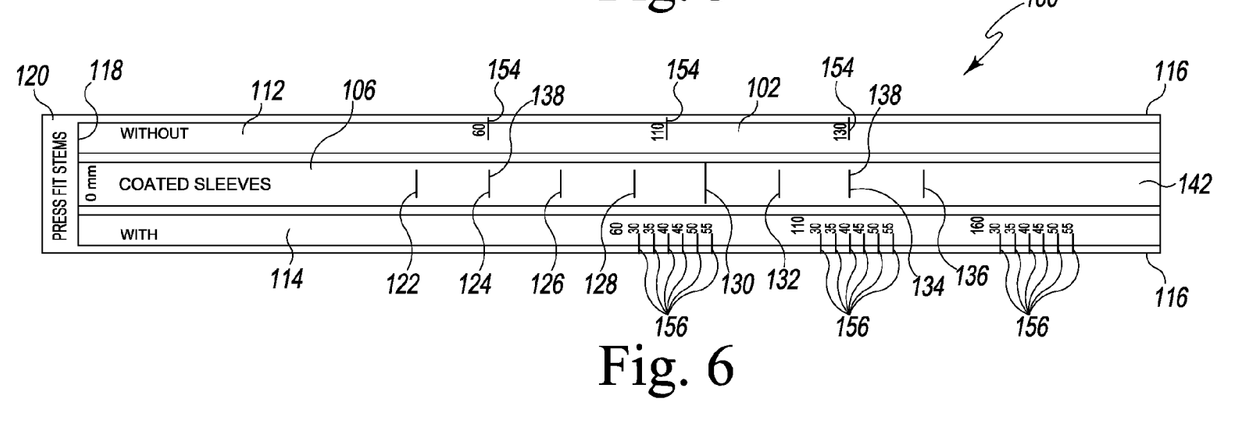

A femoral implant reference guide 100 is shown in FIGS. 4-6. The femoral implant reference guide 100 includes an elongated guide body 102 having a pair of opposed planar faces 104, 106. The guide body 102 also has a number of edge faces 108, 110, 112, 114 that extend outwardly from the planar faces 104, 106 at an oblique angle. In particular, the edge faces 108 and 110 extend at an oblique angle outwardly for the planar face 104, with the edge faces 112, 114 extending at an oblique angle outwardly for the planar face 106. The edge faces are connect by a pair of round outer surfaces 116 thereby giving the guide body 102 a generally "bow tie" cross sectional shape.

A round base 120 is formed in the distal end of the guide body 102. The round base 120 has an upper support surface 118 that is configured to support the sharp cutting tip 68 of the canal reamer 60 when the reamer is positioned on the femoral implant reference guide 100 (see FIG. 7). As such, the upper support surface 118 of the round base 120 is arranged in a direction that is orthogonal to the longitudinal axis of the guide body. More specifically, the upper support surface 118 of the round base extends annularly away from the planar faces 104, 106 of the guide body 102 in a direction that is orthogonal to the planar faces 104, 106.

As can be seen in FIGS. 5 and 6, each of the planar faces 104, 106 has a number of depth marks 122, 124, 126, 128, 130, 132, 134, 136 formed therein. The depth marks 122, 124, 126, 128, 130, 132, 134, 136 are identical in number and spacing to the depth marks 72, 74, 76, 78, 80, 82, 84, 86 of the canal reamer 60. As such, each of the depth marks 122, 124, 126, 128, 130, 132, 134, 136 corresponds to a different depth to which the canal reamer 60 may be advanced to prepare the patient's intramedullary canal for one of a number of different stem components 18.

The depth marks 122, 124, 126, 128, 130, 132, 134, 136 may be embodied as linear grooves 138 molded, etched, engraved, or otherwise formed in the in the planar faces 104, 106 of the implant reference guide's body 102. Similarly to the canal reamer 60, in an illustrative embodiment, the depth mark 130 near the middle of the guide body 102 may be colored (e.g., black) so as to distinguish it from the other depth marks 122, 124, 126, 128, 132, 134, 136. In such a way, the surgeon can use the center depth mark 130 as a quick reference guide for identifying the other depth marks 122, 124, 126, 128, 132, 134, 136. For example, the surgeon can quickly and easily identify the depth mark 124 as being "three depth marks below" the colored middle depth mark 130, or the depth mark 134 as being "two depth marks above" the colored middle depth mark 130.

Alternatively, each of the depth marks 122, 124, 126, 128, 130, 132, 134, 136 may be embodied in a different color than the other depth marks 122, 124, 126, 128, 130, 132, 134, 136. In other words, each of the depth marks 122, 124, 126, 128, 130, 132, 134, 136 may have a unique color. In such an embodiment, each of the depth marks 122, 124, 126, 128, 130, 132, 134, 136 has the same color as the corresponding depth mark 72, 74, 76, 80, 82, 84, 86 of the canal reamer 60. For example, the depth marks 72, 122 may be the same color, the depth marks 74, 124 may be the same color, the depth marks 76, 126 may be the same color, etcetera.

In embodiments in which one or more of the depth marks 122, 124, 126, 128, 130, 132, 134, 136 are colored, the grooves 138 of the colored depth mark are filled with an epoxy ink of the desired color.

As can be seen in FIGS. 5 and 6, each side 140, 142 of the femoral implant reference guide 100 corresponds to a different type of stem component 18 of the knee prosthesis 10. For example, as can be seen in FIG. 5, one side 140 of the femoral implant reference guide 100 is used to reference cemented stem components 18, with the other side 142 of the femoral implant reference guide 100 being used to reference cementless or "press-fit" stem components 18 (see FIG. 6). The planar face 104 and the edge faces 108, 110 are formed in the side 140 of the femoral implant reference guide 100, with the other planar face 106 and edge faces 112, 114 being formed in the opposite side 142 of the femoral implant reference guide 100.

As shown in FIG. 5, the edge surfaces 108, 110 include a number of size marks 144, 146, respectively, corresponding to different lengths of cemented stem components 18, including the length of such cemented stem components 18 when used with an optional femoral sleeve component (not shown). In particular, the size marks 144 of the edge surface 108 correspond to the various sizes of cemented stem components 18 themselves (i.e., without an additional sleeve component), whereas the size marks 146 of the other edge surface 110 correspond to the various sizes of cemented stem components 18 when used in conjunction with an optional sleeve component.

The opposite side 142 of the femoral implant reference guide 100 is similarly arranged, as shown in FIG. 6, only it relates to cementless or "press-fit" stem components 18. In particular, the edge surfaces 112, 114 include a number of size marks 154, 156, respectively, corresponding to different lengths of cementless stem components 18, including the length of such cementless stem components 18 when used with an optional femoral sleeve component (not shown). In particular, the size marks 154 of the edge surface 112 correspond to the various sizes of cementless stem components 18 themselves (i.e., without an additional sleeve component), whereas the size marks 156 of the other edge surface 114 correspond to the various sizes of cementless stem components 18 when used in conjunction with an optional sleeve component. As can be seen, in the case of cementless stem components 18, a number of additional size marks 156 are used within each size of stem component 18 to designate the combination of that particular size of cementless stem component 18 with any one of a number of differently-sized optional sleeve components.

The surgeon may use the femoral implant reference guide 100 to correlate a particular type and size of stem component 18 (including the optional inclusion of a sleeve component) with one of the depth marks 72, 74, 76, 78, 80, 82, 84, 86 of the canal reamer 60. In particular, the surgeon may determine the type and size of stem component 18 (along with whether or not an optional sleeve component is to be used in conjunction with it) through preoperative planning in which, amongst other things, a CT scan or other type of preoperative image may be obtained, or by the use of intraoperative adjustments to the preoperative plan. In either case, once the surgeon has determined the type and size of stem component 18 (along with whether or not an optional sleeve component is to be used in conjunction with it), the surgeon first turns the femoral implant reference guide 100 to the side 140, 142 correlating to the type of stem component 18 to be used. In particular, the surgeon turns the femoral implant reference guide 100 to the side 140 to reference cemented stem components 18, or the other side 142 to reference cementless or "press-fit" stem components 18.

Once the femoral implant reference guide 100 has been turned to the desired side 140, 142, the surgeon then locates the selected size of stem component 18 along one of the edge faces based on whether or not an optional sleeve component is being used with the selected stem component 18. For example, if the surgeon has selected a cemented stem component 18 for implantation (and hence has turned the femoral implant reference guide 100 to view its corresponding side 140), the size marks 144 of the edge surface 108 correspond to the various sizes of cemented stem components 18 themselves (i.e., without an additional sleeve component), whereas the size marks 146 of the other edge surface 110 correspond to the various sizes of cemented stem components 18 when used in conjunction with an optional sleeve component. Alternatively, if the surgeon has selected a cementless stem component 18 for implantation (and hence has turned the femoral implant reference guide 100 to view its corresponding side 142), the size marks 154 of the edge surface 112 correspond to the various sizes of cementless stem components 18 themselves (i.e., without an additional sleeve component), whereas the size marks 156 of the other edge surface 114 correspond to the various sizes of cementless stem components 18 when used in conjunction with an optional sleeve component.

Once the surgeon has determined and identified the size mark 144, 146, 154, or 156 corresponding to the type and size of stem component 18 to be implanted in the patient's femur (along with whether or not an optional sleeve component is to be used in conjunction with it), the surgeon then identifies the depth mark 122, 124, 126, 128, 130, 132, 134, 136 formed in the femoral implant reference guide 100 that is closest in location to the selected size mark 144, 146, 154, or 156. In other words, the surgeon identifies the depth mark 122, 124, 126, 128, 130, 132, 134, 136 that is closest in location to the selected size mark 144, 146, 154, or 156. In doing so, if the selected size mark 144, 146, 154, or 156 is located between a pair of depth marks 122, 124, 126, 128, 130, 132, 134, 136, the surgeon may opt for the "deeper" depth mark (even if the selected size mark is closer to the "shallower" depth mark) to ensure proper seating of the stem component 18 within the intramedullary canal.

Once the surgeon has identified the corresponding depth mark 122, 124, 126, 128, 130, 132, 134, 136 formed in the femoral implant reference guide 100, the surgeon may then correlate the identified depth mark to the canal reamer 60. The surgeon may do so in a couple different manners. Firstly, the surgeon may simply identify the depth mark 72, 74, 76, 78, 80, 82, 84, 86 of the canal reamer 60 that corresponds in location with the identified depth mark 122, 124, 126, 128, 130, 132, 134, 136 formed in the femoral implant reference guide 100. For example, if the surgeon identified the "fourth" depth mark 128 formed in the femoral implant reference guide 100, the surgeon may then correlate such an identified depth mark to the "fourth" depth mark 78 of the canal reamer 60. If the depth mark 130 near the middle of the guide body 102 is colored (e.g., black) so as to distinguish it from the other depth marks 122, 124, 126, 128, 132, 134, 136, the surgeon may use the center depth mark 130 as a quick reference guide to quickly and easily identify, for example, the depth mark 124 as being "three depth marks below" the colored middle depth mark 130, or the depth mark 134 as being "two depth marks above" the colored middle depth mark 130. If the corresponding depth mark 80 of the canal reamer 60 is also colored, the same method may be used to transfer the identified depth mark from the femoral implant reference guide 100 to the canal reamer 60. Yet further, if each of the depth mark 122, 124, 126, 128, 130, 132, 134, 136 formed in the femoral implant reference guide 100 has a unique color that correlates with the corresponding depth mark 72, 74, 76, 78, 80, 82, 84, 86 of the canal reamer 60, the surgeon may transfer the identified depth mark from the femoral implant reference guide 100 to the canal reamer 60 by selecting the depth mark of the same color on the canal reamer 60 (e.g., if the surgeon identifies a green depth mark on the femoral implant reference guide 100, then the surgeon simply identifies the green depth mark on the canal reamer 60).

Figure 7:
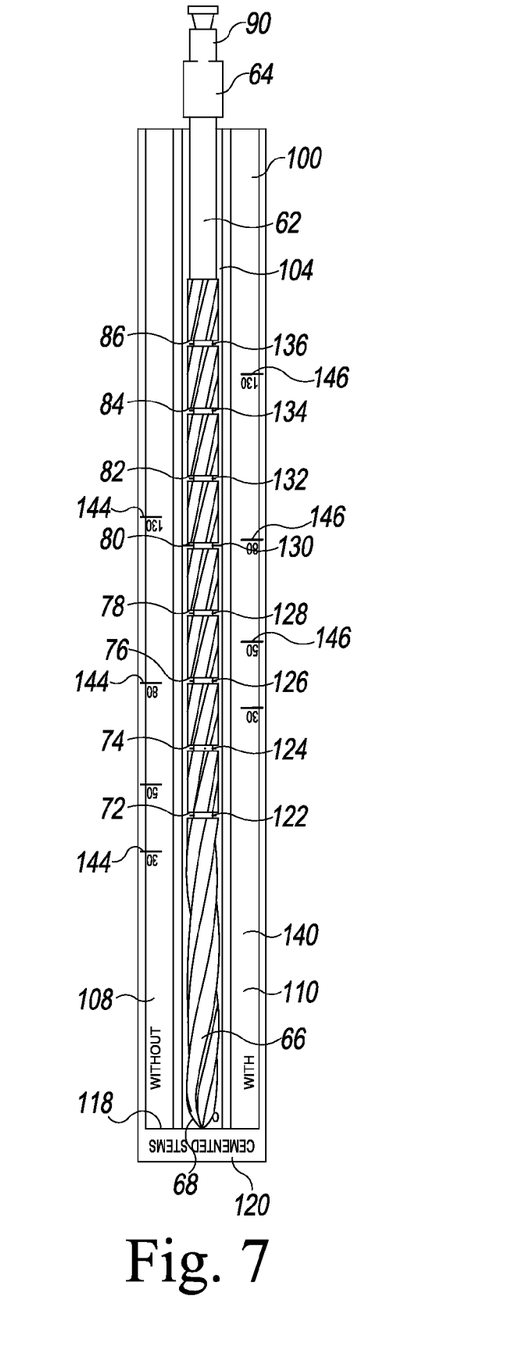
FIG. 7 is a side elevation view showing the canal reamer being correlated with the femoral implant reference guide.

Alternatively, the surgeon may actually position the canal reamer 60 on the femoral implant reference guide 100 to transfer the selected depth mark. In particular, as shown in FIG. 7, the surgeon may place the sharp cutting tip 68 of the canal reamer 60 on the upper support surface 118 of the round base 120 formed in the distal end of the guide body 102. When so positioned, the depth marks 72, 74, 76, 78, 80, 82, 84, 86 of the canal reamer 60 align with the depth marks 122, 124, 126, 128, 130, 132, 134, 136 of the femoral implant reference guide 100. As such, the surgeon may correlate the identified the size mark 144, 146, 154, or 156 corresponding to the type and size of stem component 18 to be implanted in the patient's femur (along with whether or not an optional sleeve component is to be used in conjunction with it) directly to the depth marks 72, 74, 76, 78, 80, 82, 84, 86 of the canal reamer 60.

Once the surgeon has determined the selected depth mark 72, 74, 76, 78, 80, 82, 84, 86 of the canal reamer 60 to be used, the surgeon then reams the intramedullary canal of the patient's femur. In particular, the surgeon uses the canal reamer 60 to ream the portion of the patient's intramedullary canal into which the stem component 18 is implanted. The canal reamer 60 produces a bore possessing the final geometry (i.e., the shape) required to accept the selected stem component 18 of the knee prosthesis 10. Based on the desired diameter of the stem component 18 identified during a preoperative templating process, the surgeon first selects an appropriate starting size of the canal reamer 60 to be used. In particular, as discussed above, the canal reamer 60 may be provided in 1 mm diameter increments ranging from 8 mm to 24 mm.

Depending on the size of the intramedullary canal of the patient's femur, the surgeon selects and attaches a canal reamer 60 having an appropriately-sized starting diameter to the chuck of the rotary power tool. The surgeon then inserts the cutting head 66 of the canal reamer 60 into the intramedullary canal of the patient's femur and activates the power tool. The power tool rotates the canal reamer 60 thereby causing its cutting flutes 70 to ream or otherwise cut the bone tissue of the femur. The canal reamer 60 is advanced deeper into the intramedullary canal of the patient's femur until the desired depth mark 72, 74, 76, 78, 80, 82, 84, 86 aligns with a surgically-prepared planar surface of the distal femur.

The initial canal reamer 60 is then removed from the power tool and the reamer 60 with the next larger diameter is then attached to the power tool and the process repeated. The surgeon progressively reams with increasingly larger canal reamers 60 until the desired surgical bore is obtained.

A tibial implant reference guide 200 is shown in FIGS. 8-11. The tibial implant reference guide 200 is essentially the same as the femoral implant reference guide 100, only it is three-sided instead of two-sided. As such, in addition to the planar faces 104, 106, its elongated guide body 102 includes an additional planar face 204 and a pair of additional edge faces 208, 210 that extend outwardly from the planar face 204 at an oblique angle. The additional planar face 204 of the tibial implant reference guide 200 has the number of depth marks 122, 124, 126, 128, 130, 132, 134, 136 formed therein in a similar manner to the other faces 104, 106, with the additional edge faces 208, 210 having a number size marks 244, 246, respectively, corresponding to different lengths of cemented and cementless stem components 18.

Figure 9:
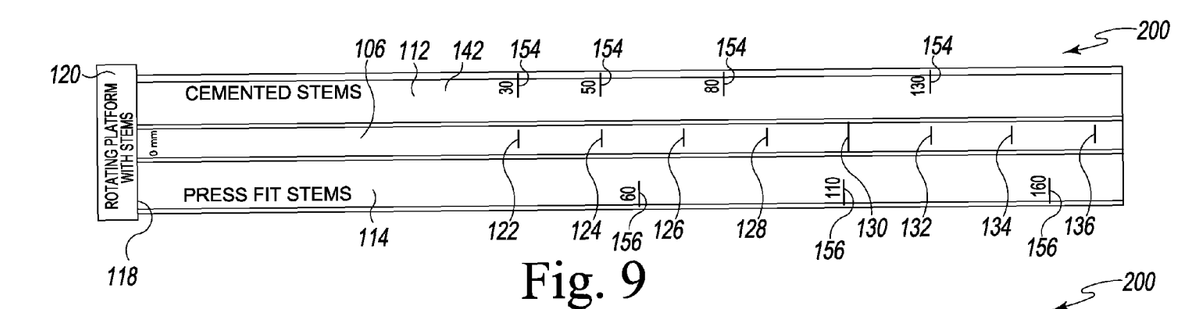
FIGS. 9-11 are side elevation views of the tibial implant reference guide of FIG. 8.
Figure 10:
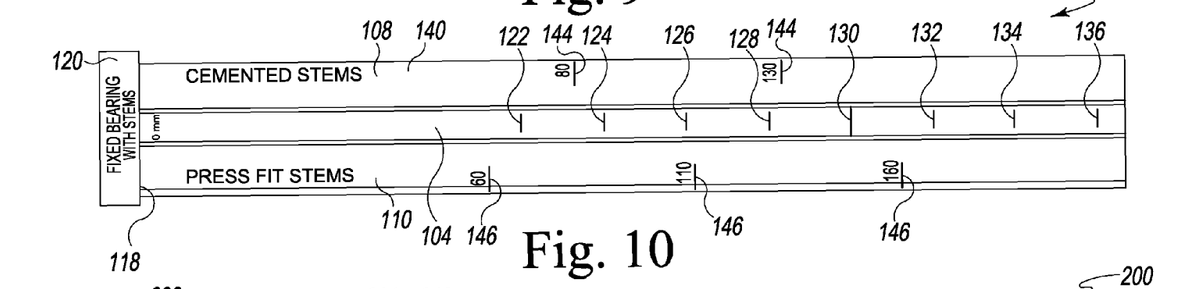
Figure 11:
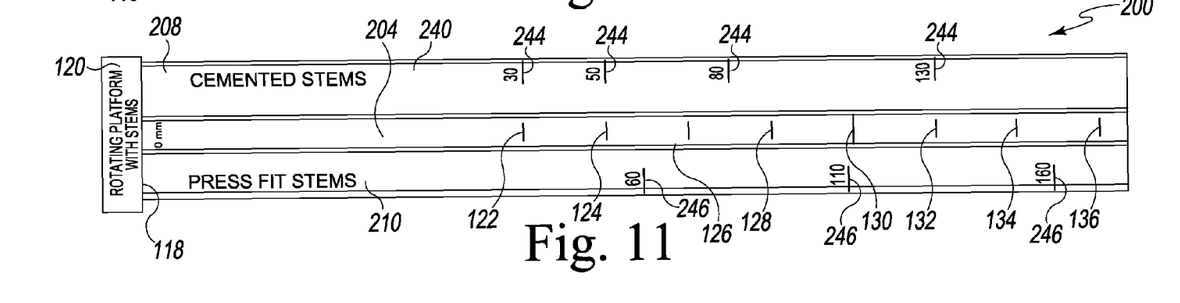

As can be seen in FIGS. 9-11, each side 140, 142, 240 of the tibial implant reference guide 200 corresponds to a different type of component configuration utilizing the stem component 18 of the knee prosthesis 10. For example, as can be seen in FIG. 10, one side 140 of the tibial implant reference guide 200 is used to reference fixed-bearing tibial trays 14 with both cemented and cementless stem components 18, whereas another side 142 of the tibial implant reference guide 200 is used to reference rotating-bearing tibial trays 14 with both cemented and cementless stem components 18 (see FIG. 9). As shown in FIG. 11, the remaining side 240 of the tibial implant reference guide 200 is used to reference both fixed- and rotating-bearing tibial trays 14 with both cemented and cementless stem components 18 and in conjunction with an optional sleeve component.

In a similar manner to as described above in regard to the femoral implant reference guide 100, the surgeon may use the tibial implant reference guide 200 to correlate a particular type and size of stem component 18 (including the optional inclusion of a sleeve component) with one of the depth marks 72, 74, 76, 78, 80, 82, 84, 86 of the canal reamer 60. In particular, the surgeon may determine the type of tibial tray 14 (i.e., fixed-bearing tray or rotating-bearing tray) and the type and size of stem component 18 (along with whether or not an optional sleeve component is to be used in conjunction with it) through preoperative planning in which, amongst other things, a CT scan or other type of preoperative image may be obtained, or by the use of intraoperative adjustments to the preoperative plan. In either case, once the surgeon has determined the type of tibial tray 14 and the type and size of stem component 18 (along with whether or not an optional sleeve component is to be used in conjunction with it), the surgeon turns the tibial implant reference guide 200 to the side 140, 142, 240 correlating to the type of tibial tray 14 and the type of stem component 18 to be used. In particular, the surgeon turns the tibial implant reference guide 200 to the side 140 to reference fixed-bearing tibial trays 14 with both cemented and cementless stem components 18, or the side 142 to reference rotating-bearing tibial trays 14 with both cemented and cementless stem components 18, or the remaining side 240 to reference both fixed- and rotating-bearing tibial trays 14 with both cemented and cementless stem components 18 and in conjunction with an optional sleeve component.

Once the tibial implant reference guide 200 has been turned to the desired side 140, 142, 240 the surgeon then locates the size mark 144, 146, 154, 156, 244, or 246 correlating to the selected size of stem component 18 along one of the edge faces in a similar manner to as described above in regard to the femoral implant reference guide 100. The surgeon then identifies the depth mark 122, 124, 126, 128, 130, 132, 134, 136 formed in the tibial implant reference guide 200 that is closest in location to the selected size mark 144, 146, 154, 156, 244, or 246. In other words, the surgeon identifies the depth mark 122, 124, 126, 128, 130, 132, 134, 136 that is closest in location to the selected size mark 144, 146, 154, 156, 244, or 246. In doing so, if the selected size mark 144, 146, 154, 156, 244, or 246 is located between a pair of depth marks 122, 124, 126, 128, 130, 132, 134, 136, the surgeon may opt for the "deeper" depth mark (even if the selected size mark is closer to the "shallower" depth mark) to ensure proper seating of the stem component 18 within the intramedullary canal.

Figure 8:
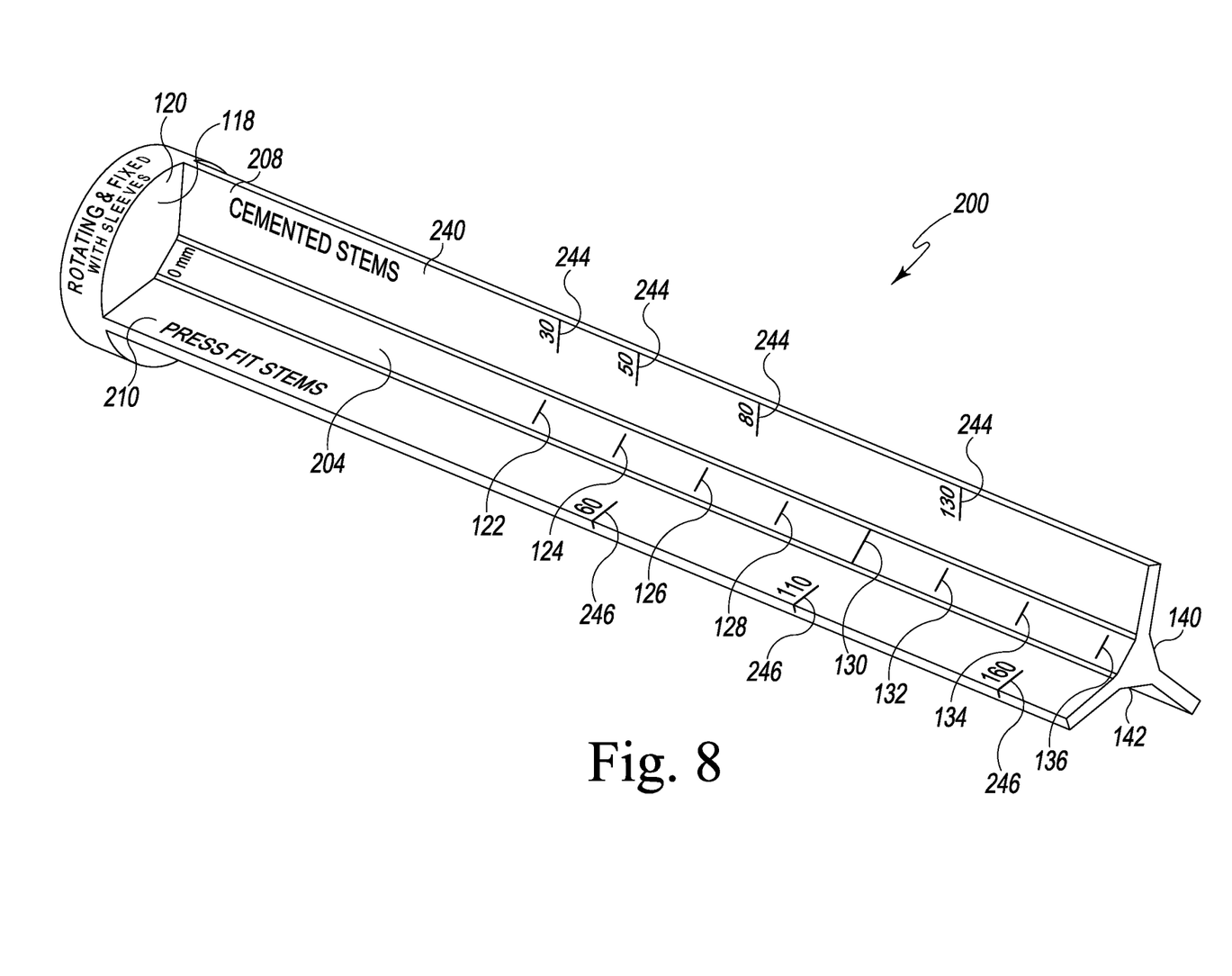
FIG. 8 is a perspective view of a tibial implant reference guide.

Once the surgeon has identified the corresponding depth mark 122, 124, 126, 128, 130, 132, 134, 136 formed in the tibial implant reference guide 200, the surgeon may then correlate the identified depth mark to the depth marks 72, 74, 76, 78, 80, 82, 84, 86 of the canal reamer 60 of the canal reamer 60 similarly to as described above in regard to the femoral implant reference guide 100.

Once the surgeon has determined the selected depth mark 72, 74, 76, 78, 80, 82, 84, 86 of the canal reamer 60 to be used, the surgeon then reams the intramedullary canal of the patient's tibia. In particular, the surgeon uses the canal reamer 60 to ream the portion of the patient's intramedullary canal into which the stem component 18 is implanted. The canal reamer 60 produces a bore possessing the final geometry (i.e., the shape) required to accept the selected stem component 18 of the knee prosthesis 10. Based on the desired diameter of the stem component 18 determined during a preoperative templating process, the surgeon first selects an appropriate starting size of the canal reamer 60 to be used. In particular, as discussed above, the canal reamer 60 may be provided in 1 mm diameter increments ranging from 8 mm-24 mm.

Depending on the size of the intramedullary canal of the patient's tibia, the surgeon selects and attaches a canal reamer 60 having an appropriately-sized starting diameter to the chuck of the rotary power tool. The surgeon then inserts the cutting head 66 of the canal reamer 60 into the intramedullary canal of the patient's tibia and activates the power tool. The power tool rotates the canal reamer 60 thereby causing its cutting flutes 70 to ream or otherwise cut the bone tissue of the tibia. The canal reamer 60 is advanced deeper into the intramedullary canal of the patient's tibia until the desired depth mark 72, 74, 76, 78, 80, 82, 84, 86 aligns with a surgically-prepared planar surface of the proximal tibia.

The initial canal reamer 60 is then removed from the power tool and the reamer 60 with the next larger diameter is then attached to the power tool and the process repeated. The surgeon progressively reams with increasingly larger canal reamers 60 until the desired surgical bore is obtained.

While the disclosure has been illustrated and described in detail in the drawings and foregoing description, such an illustration and description is to be considered as exemplary and not restrictive in character, it being understood that only illustrative embodiments have been shown and described and that all changes and modifications that come within the spirit of the disclosure are desired to be protected.

There are a plurality of advantages of the present disclosure arising from the various features of the apparatus, system, and method described herein. It will be noted that alternative embodiments of the apparatus, system, and method of the present disclosure may not include all of the features described yet still benefit from at least some of the advantages of such features. Those of ordinary skill in the art may readily devise their own implementations of the apparatus, system, and method that incorporate one or more of the features of the present invention and fall within the spirit and scope of the present disclosure.

The invention claimed is:

1. A surgical instrument system for use during a surgical procedure to implant an orthopaedic knee prosthesis, comprising:
    a surgical reamer comprising an elongated shank having (i) a proximal end configured to fit into the chuck of a rotary power tool, (ii) a cutting head located at an opposite, distal end of the shank, the cutting head comprising a cutting tip with a plurality of helical cutting flutes extending away from the cutting tip in a direction toward the proximal end of the elongated shank, and (iii) a plurality of depth marks formed in the helical cutting flutes of the cutting head, wherein each of the plurality of depth marks comprises an annular-shaped groove formed in the helical cutting flutes and is positioned at a location on the cutting head corresponding to a predetermined depth of operation of the surgical reamer, and
    an implant reference guide comprising (i) an elongated guide body having a longitudinal axis, (ii) a plurality of size marks defined on the guide body, wherein each of the plurality of size marks is positioned at a location along the longitudinal axis corresponding to a size and a type of a surgical component of the orthopaedic knee prosthesis, (iii) a plurality of depth marks defined on the guide body, wherein each of the plurality of depth marks is positioned at a location on the longitudinal axis corresponding to one of the plurality of depth marks formed in the helical cutting flutes of the cutting head of the surgical reamer, and (iv) a base formed in a distal end of the guide body, the base having a proximal-facing support surface that extends in a direction orthogonal to the longitudinal axis of the guide body,
    wherein when the surgical reamer is aligned parallel to the longitudinal axis of the implant reference guide, the proximal-facing support surface of the base is configured to engage the cutting tip of the distal end of the surgical reamer.

2. The surgical instrument system of claim 1, wherein:

the plurality of depth marks of the surgical reamer includes a first depth mark, a second depth mark, and a third depth mark, the first depth mark of the surgical reamer has a different color than the second and third depth marks of the surgical reamer, the second depth mark of the surgical reamer is located between the first depth mark of the surgical reamer and the proximal end of the elongated shank, and the third depth mark of the surgical reamer is located between the first depth mark of the surgical reamer and the distal end of the elongated shank.

3. The surgical instrument system of claim 2, wherein:

the plurality of depth marks of the surgical reamer further includes a fourth depth mark and a fifth depth mark, the fourth depth mark of the surgical reamer is located between the second depth mark and the proximal end of the elongated shank, and the fifth depth mark of the surgical reamer is located between the third depth mark and the distal end of the elongated shank.

4. The surgical instrument system of claim 1, wherein each of the plurality of depth marks of the surgical reamer has a different color than the other depth marks of the surgical reamer.

5. The surgical instrument system of claim 4, wherein each of the number of the plurality of depth marks is filled with a colored epoxy ink.

6. The surgical instrument system of claim 1, wherein the annular-shaped groove formed in the helical cutting flutes of each of the plurality of depth marks of the surgical reamer extends around the entire circumference of the elongated shank of the surgical reamer.

7. A method of performing an orthopaedic surgical procedure to implant a prosthetic knee component into an end of a long bone of a knee of a patient, comprising:

determining a size of the prosthetic component to implant into the end of the long bone of the knee of the patient, identifying a size mark corresponding to the determined size of the prosthetic component from a plurality of size marks located on an implant reference guide having a longitudinal axis and a base that includes a support surface that extends orthogonal to the longitudinal axis, determining a depth mark, from a plurality of depth marks located on the implant reference guide, that is located closest to the size mark identified as corresponding to the determined size of the prosthetic component, engaging a cutting tip of a surgical reamer with the support surface of the implant reference guide, aligning the surgical reamer parallel to a longitudinal axis of the implant reference guide with the cutting tip engaged with the support surface of the implant reference guide, with the cutting tip engaged with the support surface of the implant reference guide, identifying a depth mark, from a plurality of depth marks located on the surgical reamer, that corresponds to the determined depth mark on the implant reference guide, and advancing the surgical reamer into the intramedullary canal of the long bone of the patient to a depth which corresponds to the identified depth mark on the surgical reamer.

8. The method of claim 7, wherein:

determining the size of the prosthetic component to implant into the end of the long bone of the knee of the patient comprises determining a size of a stem component to implant into a proximal end of a tibia of the patient, and advancing the surgical reamer comprises advancing the surgical reamer into the intramedullary canal of the tibia of the patient to a depth which corresponds to the identified depth mark on the surgical reamer.

9. The method of claim 7, wherein:

determining the size of the prosthetic component to implant into the end of the long bone of the knee of the patient comprises determining a size of a stem component to implant into a distal end of a femur of the patient, and advancing the surgical reamer comprises advancing the surgical reamer into the intramedullary canal of the femur of the patient to a depth which corresponds to the identified depth mark on the surgical reamer.

\* \* \* \* \*